United States Patent
Scott et al.

[11] Patent Number: 5,637,502
[45] Date of Patent: Jun. 10, 1997

[54] ENHANCED ATTRITION BIOREACTOR FOR ENZYME HYDROLYSIS OF CELLULOSIC MATERIALS

[75] Inventors: Timothy C. Scott, Knoxville; Charles D. Scott, Oak Ridge; Brendlyn D. Faison; Brian H. Davison, both of Knoxville; Jonathan Woodward, Oak Ridge, all of Tenn.

[73] Assignee: Lockheed Martin Energy Systems, Inc., Oak Ridge, Tenn.

[21] Appl. No.: 591,272

[22] Filed: Jan. 25, 1996

Related U.S. Application Data

[60] Division of Ser. No. 239,638, May 9, 1994, Pat. No. 5,508,183, which is a continuation-in-part of Ser. No. 884,506, May 15, 1992, Pat. No. 5,348,871.

[51] Int. Cl.$^6$ .................................................... C12M 3/00
[52] U.S. Cl. ............................ 435/297.1; 422/234
[58] Field of Search ........................ 422/140, 234, 422/225; 241/46.17; 435/161, 162, 163, 165, 262, 276, 277, 209, 105, 297.1

[56] References Cited

U.S. PATENT DOCUMENTS

| | | | |
|---|---|---|---|
| 5,248,484 | 9/1993 | Scott et al. | 422/225 |
| 5,270,189 | 12/1993 | Scott et al. | 435/139 |
| 5,348,871 | 9/1994 | Scott et al. | 435/165 |

OTHER PUBLICATIONS

Riley, R. "Reverse Osmosis" *Membrane Separation Systems* Apr. 1990 vol. 2 U.S. D.O.E. Office of Energy Research.
Wright et al. "Simultaneous Saccharification and Fermentation of Lignocellulose" The Human Press 1988 pp. 75–90.

*Primary Examiner*—David A. Redding
*Attorney, Agent, or Firm*—Preston H. Smirman

[57] ABSTRACT

A process for converting cellulosic materials, such as waste paper, into fuels and chemicals, such as sugars and ethanol, utilizing enzymatic hydrolysis of the major carbohydrate of paper: cellulose. A waste paper slurry is contacted by cellulase in an agitated hydrolyzer. An attritor and a cellobiase reactor are coupled to the agitated hydrolyzer to improve reaction efficiency. Additionally, microfiltration, ultrafiltration and reverse osmosis steps are included to further increase reaction efficiency. The resulting sugars are converted to a dilute product in a fluidized-bed bioreactor utilizing a biocatalyst, such as microorganisms. The dilute product is then concentrated and purified.

5 Claims, 1 Drawing Sheet

ENHANCED ATTRITION BIOREACTOR FOR ENZYME HYDROLYSIS OF CELLULOSIC MATERIALS

CROSS REFERENCE TO RELATED APPLICATION

This application is a division of application Ser. No. 08/239,638 filed May 9, 1994, now U.S. Pat. No. 5,508,183, which is a continuation-in-part application under 37 C.F.R. § 1.53 of U.S. patent application Ser. No. 07/884,506, filed on May 15, 1992 now U.S. Pat. No. 5,348,871, the entire disclosure of which is incorporated herein by reference.

This invention was made with Government support under Contract No. DE-AC05-84OR21400 awarded by the U.S. Department of Energy to Martin Marietta Energy Systems, Inc. and the Government has certain rights in this invention. This invention was funded through the Office of Conservation and Renewable Energy.

FIELD OF THE INVENTION

This invention relates to the conversion of cellulosic materials into fuels and chemicals, and more particularly to a bioprocessing system employing enzymatic hydrolysis of the major carbohydrates in paper: cellulose and hemicellulose.

BACKGROUND OF THE INVENTION

Waste materials, particularly solid wastes, from various sources are continuing to increase at the same time that disposal of such material is becoming more difficult and expensive. As a result, there is increasing interest in recycling useful components of wastes and in using certain fractions for production of energy or higher-value materials such as commodity chemicals. The growing interest in segregation of solid waste, frequently at the source, will potentially provide relatively well-defined materials that are prime candidates for other uses. Of particular interest is the large amount of cellulosic materials, already segregated, that could be considered as low-cost, perhaps even negative cost, feed materials for the production of sugars and various other useful chemicals such as alcohols, neutral solvents and organic acids. Cellulosic materials are defined as those materials which contain cellulose. Cellulosic materials include wood, woody pulp, woody biomass, paper, cardboard, and related materials. As a result of recycling, the problem of disposal of solid wastes would be partially alleviated.

Solid waste material from residential and industrial sources represent a heterogenous mixture that is predominantly made up of metals, glass, plastics, food residues, and paper products. Although conservation efforts have had a significant impact, the volume of this material remains quite large and will probably continue to increase in the foreseeable future. A large amount of this material is either deposited in landfills or incinerated, whereas only a small amount is recycled or further used. Due to environmental restrictions and a lack of suitable new sites, disposal by landfill or incineration is becoming prohibitively expensive or even impossible in certain areas.

It has been estimated that half of municipal solid waste is made up of paper, with the other half consisting of glass, plastics, metals and other materials. A significant portion of the waste paper is comprised of newsprint. Large fractions of various types of the solid waste materials could be effectively recycled if fractionation and segregation of the components was carried out. Although there is some technology available that will fractionate mixed waste, there appears to be a trend towards segregation by the generator. If this occurs on a large scale, materials that are not readily recycled could well be considered as relatively well-defined feed materials for further processing.

Segregated waste paper products could be an ideal feed material for biological conversion to sugars (conversion of cellulose and hemicellulose) or aromatic compounds (conversion of lignin) with the possibility of subsequent conversion to a variety of useful chemicals. Of particular interest would be the production of organic acids, neutral solvents and various alcohols as chemical intermediates.

Waste paper is made up of three primary constituents: cellulose (~61%), hemicellulose (~16%), and lignin (~21%). The first two, cellulose and hemicellulose, are complex carbohydrates that can be hydrolyzed to the monomer sugars, glucose and xylose by use of the appropriate enzyme systems. The primary sugar is glucose which represents an intermediate product that can also be converted to chemicals such as ethanol by a fermentation process. The process chemistry of interest is listed below:

Over-all Cellulose Hydrolysis to Glucose

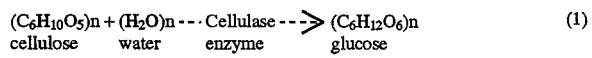
(1)

Cellobiose Formation (an inhibiting intermediate product)

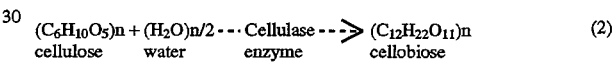
(2)

Hydrolysis of Cellobiose to Glucose

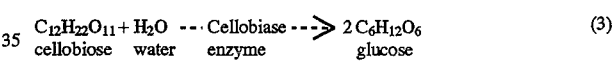
(3)

Bioconversion of Glucose to Ethanol

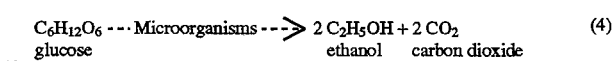
(4)

Unless extensive purification is carried out, the usual cellulase enzymes (a crude extract from specific microorganisms) include a mixture that has several functions including those biocatalysts that interact with the end groups of the cellulose polymer, those biocatalysts that interact with the interior part of the cellulose molecule, and those that convert cellulose to glucose. Cellobiose, an intermediate disaccharide, that is also formed (Equation 2) and glucose, both inhibit the hydrolysis reaction. Cellobiose can be converted to glucose if a sufficient quantity of the enzyme cellobiase is present (Equation 3). Cellobiase is also a constituent of the crude mixture of the cellulase enzymes but it is usually present at a relatively low concentration. In order to enhance the overall hydrolysis process, exposure to additional cellobiase would be highly beneficial. Lignin is a polymeric structure of aromatic compounds which can be oxidized to a series of useful chemical compounds, but this technology is not well-developed as yet, so that residue could be used as a fuel for producing steam.

Research on saccharification processes for the conversion of cellulose to glucose have taken two major approaches. Acid hydrolysis is attractive since it is relatively rapid. However, the acid processes also produce chemicals other than sugar that represent a process loss or complication. Treating the acid effluent or recovery of the excess acid also presents problems. On the other hand, the enzymatic approach is much more specific with a higher yield but, until recently, there has been concern over the length of time for the reaction and the potential high cost of the biocatalyst since there was no processing scheme for recovery and reuse. Both of the shortcomings of the enzyme process now appear to be solved so it is the obvious choice for new process development. The bioprocessing system of the present application is centered around the enzymatic hydrolysis of a major fraction of the cellulose in paper by the use of cellulase to produce sugar. Various intermediate processing steps involving ultrafiltration and reverse osmosis will be utilized to increase the overall reaction efficiency. Finally, subsequent fermentation will be carried out on the resulting sugar to chemicals, with a preliminary emphasis on useful chemicals such as ethanol.

OBJECTS OF THE INVENTION

Accordingly, it is an object of the present invention to provide a new and improved process for recycling cellulosic materials.

It is another object of the present invention to provide a new and improved process for producing fuels and chemicals, such as ethanol.

It is another object of the present invention to provide a new and improved process for reducing the cost of solid waste disposal.

Further and other objects of the present inventions will become apparent from the description contained herein.

SUMMARY OF THE INVENTION

In accordance with one aspect of the present invention, the foregoing and other objects are achieved by:

shredding the cellulosic material to increase the surface area of the cellulosic material;

mixing the shredded cellulosic material with a sufficient amount of water to form a slurry;

introducing the slurry into a reaction vessel;

introducing cellulase into the reaction vessel under conditions suitable to cause a hydrolysis reaction of the cellulose, the hydrolysis reaction forming glucose and cellobiose from the cellulose;

circulating a first side stream from the reaction vessel through an attritor to form a second side stream, the first side stream containing water, cellulase, cellulosic material, glucose, and cellobiose, the attritor comprising a centrifugal pump, the attritor being in fluid communication with the reaction vessel, the attritor providing increased surface area to the cellulosic material;

circulating the second side stream from the attritor through a first filter means to form a third side stream, the first filter means being in fluid communication with the attritor and the reaction vessel, the second side stream containing water, cellulase, cellulosic material, glucose, and cellobiose, the first filter means separating the cellulosic material of the second side stream from the water, cellulase, glucose and cellobiose of the second side stream, the third side stream containing water, cellulase, glucose and cellobiose;

recycling the cellulosic material of the second side stream back to the reaction vessel;

circulating the third side stream from the first filter means through a second filter means to form a fourth side stream, the second filter means being in fluid communication with the first filter means and the reaction vessel, the third side stream containing water, cellulase, glucose and cellobiose, the second filter means separating the cellulase of the third side stream from the water, glucose and cellobiose of the third side stream, the fourth side stream containing water, glucose and cellobiose;

recycling the cellulase of the third side stream back to the reaction vessel;

circulating the fourth side stream from the second filter means through a cellobiase reactor to form a fifth side stream, the cellobiase reactor being in fluid communication with the second filter means, the cellobiase reactor comprising a fixed bed of immobilized cellobiase, the cellobiase reactor providing continuous removal of cellobiose from the fourth side stream, the cellobiase reactor converting the cellobiose of the fourth side stream to glucose, the fifth side stream containing glucose and water;

circulating the fifth side stream from the cellobiase reactor through a third filter means to form a glucose product stream, the third filter means being in fluid communication with the cellobiase reactor and the reaction vessel, the third filter means separating the glucose of the fifth side stream from the water of the fifth side stream; and recycling the water of the fifth side stream back to the reaction vessel.

In accordance with another aspect of the present invention, the foregoing and other objects are achieved by:

a first reaction vessel;

an attritor, the attritor being in fluid communication with the first reaction vessel;

a first filter means, the first filter means being in fluid communication with the attritor and the first reaction vessel;

a second filter means, the second filter means being in fluid communication with the first filter means and the first reaction vessel;

a cellobiose reactor, the cellobiose reactor being in fluid communication with the second filter means; and a third filter means, the third filter means being in fluid communication with the cellobiose reactor and the first reaction vessel.

DETAILED DESCRIPTION OF THE PREFERRED EMBODIMENTS

Figure 1:
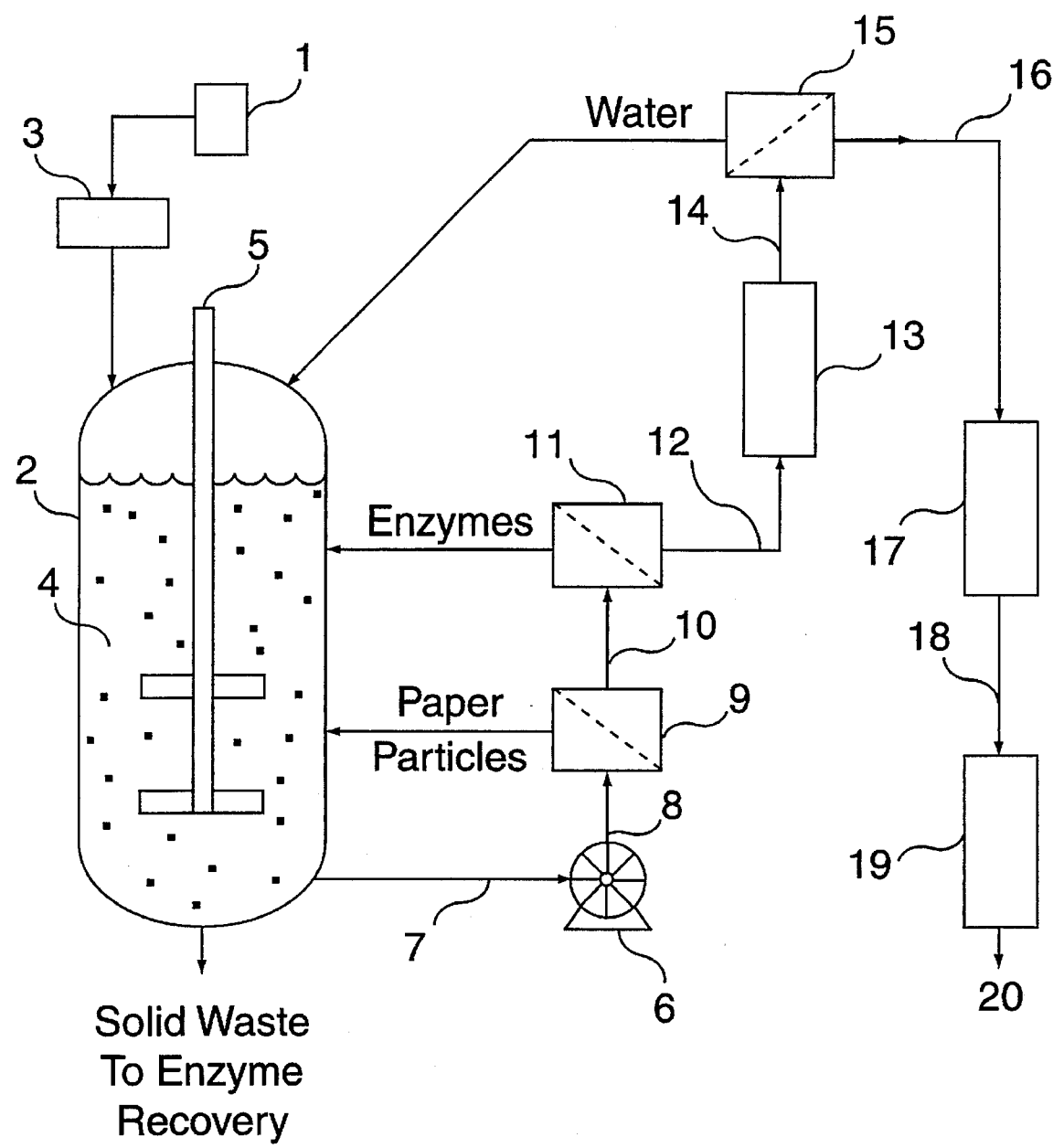
FIG. 1 is a schematic diagram of the major processing steps involved with the conversion of cellulosic materials into fuels and chemicals, in accordance with the present invention.

With reference to FIG. 1, the cellulosic material, such as waste paper 1, is introduced into the agitated hydrolyzer 2. The cellulosic material is preferably size-reduced prior to introduction into the agitated hydrolyzer 2 and prior to any chemical treatment. The cellulosic material may be initially placed into a shredder 3, or other suitable size-reducing devices, in order to provide increased surface area to the cellulosic material. Several adequate shredding systems covering a wide size range are available on the market, such as the PAPER DISINTEGRATOR™ manufactured by Jay Bee Manufacturing, Inc., Tyler, Tex. Size reduction of the waste paper 1 and the formation of an aqueous waste paper slurry 4 (pulping) will be required for further processing. The formation of an aqueous waste paper slurry 4 is accomplished by mixing the size-reduced cellulosic material with water.

While the waste paper slurry 4 is in the agitated hydrolyzer 2, it is then contacted with cellulase, which causes a hydrolysis reaction to occur. The agitated hydrolyzer 2 has at least one inlet and at least one outlet. The agitation may be provided by an internal stirring device 5, or any other suitable means. The agitated hydrolyzer 2 is usually operated according to the following parameters: a temperature in the range of about 30° to about 60° C., a cellulase concentration in the range of about 1 to about 100 international units (1 international unit (I.U.) is defined as 1 µmole/minute of glucose equivalent released), and a paper pulp concentration in the range of about 1 to about 20 wt. %.

The waste paper slurry 4 is contacted with the cellulase in the agitated hydrolyzer 2 for an sufficient amount of time for saccharification, and hence solubilization, to occur. Any solid wastes, such as non-cellulosic materials, may be removed through an outlet. In the past, such systems (agitated hydrolyzers) were designed as simple, batch-fed, stirred tanks. Reaction times of many hours or even days were required for an acceptable yield. There are two basic problems that must be overcome in order to enhance this processing step. First, it appears that part of the enzyme process requires fresh surfaces on the cellulosic material in order to maintain a high rate of interaction. Second, it is known that one of the intermediate products, cellobiose (a disaccharide) and glucose, both inhibit the further breakdown of paper to cellulose.

An attritor 6, in fluid communication with the agitated hydrolyzer 2, is used in order to constantly provide new surface area and increase the reaction efficiency. This is accomplished by introducing a first side stream 7 into the attritor 6. This first side stream 7 contains cellulase, cellulosic material, glucose, and cellobiose. The attritor 6 has at least one inlet and at least one outlet. The attritor 6 can be comprised of any means which produces a high-shear field for causing attrition or size reduction of the solid particulate. For many applications, the attritor 6 can be comprised of a high speed rotor contained in an enclosed chamber through which the first side stream 7 will pass. In many cases, a high-speed centrifugal pump can be used for this purpose. For large or particularly hard particulates, a grinder, shredder, blender, or other suitable size reduction device may be utilized in place of, or in addition to, the pump. In any case, means to circulate the reactor contents through the attritor 6 can be provided by the attritor 6 itself, or by separate circulating means, such as a diaphragm pump or other type of pump. The attritor 6 may comprise several devices in series, parallel, or complex configurations. Since the attritor 6 also mixes and circulates the reactants, a stirring device may be optional. The attritor 6 may be operated constantly or intermittently. A complete description of this technology is found in U.S. Pat. No. 5,248,484 to Scott et al., the entire disclosure of which is incorporated herein by reference.

An additional problem with reaction efficiency concerns the inhibitory effect of elevated levels of sugar (glucose) and cellobiose in the agitated hydrolyzer 2. Therefore, the levels of glucose and cellobiose in the agitated hydrolyzer 2 must be maintained at very low levels. However, operating the agitated hydrolyzer 2 with very low levels of glucose and cellobiose is not very efficient unless these materials can be continuously removed. Therefore, the present invention has modified previous reaction schemes in a way which will maintain low glucose and cellobiose concentrations in the agitated hydrolyzer 2, while removing the glucose as a product at higher concentrations.

After the first side stream 7 passes through the attritor 6 to form a second side stream 8 but prior to being introduced into a cellobiase reactor 13, the second side stream is sequentially filtered by two different filtering units to remove the cellulosic material and the enzymes for return to the agitated hydrolyzer 2. Although this filtration process could be carried out with a single ultrafilter, it has been determined that it is preferable to use a preceding microfilter to remove the larger particulates so that the ultrafilter will be less prone to plugging or fouling up with resulting inefficient operation. All the membrane filters of the present invention will operate in the cross flow mode in which there is a continuous flow of the fluid mixture past the membrane filter surface. As a result, there will not be complete removal of the smaller constituents, and small portions of these constituents will be returned to the agitated hydrolyzer 2 in the recycle streams. However, only the smaller constituents will penetrate the filter membranes and be removed for further processing.

The second side stream 8 is first introduced into a microfilter 9 (Microfilters utilize porous membranes with pore diameters from 0.1 µm to 10 µm that are usually used to filter suspended particulates. Many such filter materials are available from various manufacturers and typical of these is the CMF membrane from FilmTech Corporation, Minneapolis, Minn.) to form a third side stream 10. The second side stream 8, like the first side stream 7, also contains water, cellulase, cellulosic material, glucose and cellobiose. The third side stream 10 should only contain water, cellulase, glucose and cellobiose. The microfilter 9 is in fluid communication with the attritor 6 and the agitated hydrolyzer 2. The microfilter 9 will allow a large portion of the relatively smaller water, cellulase, glucose and cellobiose molecules in the second side stream 8 to pass through the membrane into the third side stream 10 while the relatively larger substrate particles (unreacted cellulosic material) and some residual smaller molecules are retained and ultimately returned to the agitated hydrolyzer 2 for further processing.

The third side stream 10 is then introduced into an ultrafilter 11 (Ultrafilters utilize porous membranes with pore diameters in the range of 20–1000 Angstroms that are usually used to filter dissolved macromolecules such as proteins and enzymes. Many such filter materials are available from various manufacturers and typical of these is the UF-38 membrane from FilmTech Corporation, Minneapolis, Minn.) to form a fourth side stream 12. The fourth side stream 12 should only contain water, glucose and cellobiose. The ultrafilter 11 is in fluid communication with the attritor 6 and the agitated hydrolyzer 2. The ultrafilter 11 will allow a large portion of the relatively smaller water, glucose and cellobiose molecules of the third side stream 10 to pass through while the relatively larger enzyme molecules (cellulase) and a small portion of the smaller molecules are retained and ultimately returned to the agitated hydrolyzer 2 to allow for further processing. Ultrafiltration is utilized to return the enzymes (cellulase) and a small portion of the glucose and cellobiose to the agitated hydrolyzer 2, while a separated large portion of the third side stream 10 is further processed to remove a large portion of the cellobiose and glucose. This step increases reaction efficiency in that it allows for continuous removal of a large portion of the inhibition products, glucose and cellobiose, from the agitated hydrolyzer 2. The sole purpose of the cellobiase reactor 13 is to convert the cellobiose to glucose.

Cellobiose is converted to the glucose product by utilizing a cellobiase reactor 13. The cellobiase reactor 13 is in fluid communication with the ultrafilter 11. The cellobiase reactor 13 has at least one inlet and at least one outlet. After the third side stream 10 passes through the ultrafilter 11 to form a fourth side stream 12, the fourth side stream 12 is then introduced into the cellobiase reactor 13. The cellobiase can be immobilized by adsorption of a dispersed adsorbent in a stabilized gel bead. The immobilized cellobiase can be used for extended periods without replenishment and it effectively reduces the level of cellobiose. The use of the cellobiase reactor 13 is more efficient than adding the cellobiase enzyme in free suspension into the agitated hydrolyzer 2 where it will ultimately be lost during recycle and reuse.

The fourth side stream 12 passes through the cellobiase reactor 13 to form a fifth side stream 14, which should contain only glucose and water, along with a residual amount of cellobiose (less than 1% of the glucose content). Since there is no need to further process the water, it should be returned to the agitated hydrolyzer 2, whereas the glucose should be further processed in accordance with the present invention. Additionally, if most of the water is removed from the fifth side stream 14, a highly concentrated glucose product stream 16 will be created for further processing (fermentation) in accordance with the present invention. In order to accomplish this, the fifth side stream 14 is sent through a reverse osmosis filter 15 which also will operate as a cross flow filtration unit (Reverse osmosis filters utilize porous membranes with pore diameters of 5-20 Angstroms that are usually used to separate dissolved microsolutes. Many such filter materials are available from various manufacturers and typical of these is the FT-30 membrane available from FilmTech Corporation, Minneapolis, Minn. that separates the water from the glucose. The reverse osmosis filter 15 is in fluid communication with the cellobiase reactor 13 and the agitated hydrolyzer 2. Reverse osmosis ("RO"), the first membrane-based separation process to be widely commercialized, is a separation process that utilizes a dense semipermeable membrane, highly permeable to water and highly impermeable to microorganisms, colloids, dissolved salts, and organics. Once this is done, most of the water with a only a residual amount of glucose is returned to the agitated hydrolyzer 2, while the glucose product is effectively concentrated to form a glucose product stream 16 that can be used in the fermentation step. By utilizing reverse osmosis, the glucose of the glucose product stream 16 will be sterile and relatively pure at a much higher concentration than that produced in the agitated hydrolyzer 2 by conventional means.

Fermentation of the sugar of the product stream to ethanol or other chemicals can be carried out in an fluidized-bed bioreactor 17 utilizing biocatalysts, such as immobilized microorganisms at high concentration. The fluidized-bed bioreactor 17 is in fluid communication with the reverse osmosis filter 15. If the product is to be ethanol, then immobilization of the microorganism *Zymomonas mobilis* at concentrations greater than $10^{10}$ cells per mL would be used, for example. However, other suitable microorganisms may be used in this fermentation step to produce the ethanol, such as *Saccharomyces cervisiae, Saccharomyces oviformis, Saccharomyces uvarum,* and *Saccharomyces bayanas*. Immobilization material could be various hydrocolloidal gels such as cross-linked carrageenan or modified bone gel in 1.0 to 1.5 mm-diameter gel beads. The fluidized-bed bioreactor 17 has at least one inlet and at least one outlet. The fluidized bed bioreactor 17 is operated according to the following parameters: a temperature in the range of about 25° to about 40° C., sugar concentration in the range of about 10 to about 20%, and liquid flow velocities in the range of about 0.05 to about 0.5 cm/sec.

Once the fermentation process is complete a dilute end product 18 (ethanol) is formed. Incorporation of a concentration step based on adsorption may be considered in order to concentrate the dilute end product 18. In the case of adsorption, a compatible solid sorbent could be used that has a high affinity for the end product 20. This can be accomplished by the utilization of a biparticle fluidized-bed bioreactor that allows for the combination of both fermentation and product recovery by adsorbent particles moving cocurrently or countercurrently (with respect to the fluid flow) through a fluidized bed of biocatalyst particles. The biparticle fluidized-bed bioreactor has at least one inlet and at least one outlet. A complete description of this process is found in U.S. Pat. No. 5,270,189 to Scott, the entire disclosure of which is incorporated herein by reference.

Examples of waste paper hydrolysis and ethanol production in accordance with the present invention are presented below:

EXAMPLE I

The process described herein is suitable for the enhanced hydrolysis of waste paper that includes processing of a recycle side stream. An 800 mL bioreactor with a 500 mL active volume has a side stream exiting the bioreactor, passing through a high-speed centrifugal pump and then returning to the bioreactor. The reactor contains approximately 500 mL of a slurry with 2% shredded waste paper and 80 International Units of cellulase activity per gram of paper. The system is buffered at a pH of 5.5 with a phosphate buffer and is maintained at 50° C. by an external heating jacket. The circulating side stream supplies enough agitation to keep the waste paper particles in suspension. A portion of the circulating side stream is further processed by a membrane ultrafilter to remove a portion of the accumulated glucose and cellobiose. Over a period of 25 hours, over 90% of the included cellulose is converted to glucose.

EXAMPLE II

The process described herein is suitable for the enhanced production and recovery of ethanol. *Zymomonas mobilis*, a bacterium, is immobilized in 4% carrageenan beads. The feed is 15% dextrose solution made from corn syrup and light steep water with 0.05M KCl and antifoam added. In a 3-in.-ID column the flowrate is approximately 10 L/h. The optimum process temperature is about 30° to 35° C. A sorbent second particulate phrase, such as a polystyrene resin or a hydrophobic molecular sieve such as Linde SILICALITE™ is added and removed continuously in accordance with the present invention to recover the ethanol product and prevent inhibitory buildup of the product in the reactor.

In the alternative, concentration and purification of the dilute end product 18 can be accomplished by utilizing a contactor 19. The contactor 19 being in fluid communication with the fluidized-bed bioreactor 17. The contactor 19 would contain a sorbent having a high affinity for the dilute end product 18. The dilute end product 18 is introduced into the contactor 19 containing an appropriate sorbent, the sorbent sorbs the dilute end product 18, thereby resulting in concentration and purification of the dilute end product 18 into an end product 20, which is then recovered. The contactor 19 can be either the fluidized-bed or fixed-bed type. Additionally, the contactor 19 can be arranged in a multiple configuration, with one or more contactors being active and regenerated. The contactor 19 has at least one inlet and at least one outlet.

While there has been shown and described what are at present considered the preferred embodiments of the invention, it will be obvious to those skilled in the art that various changes and modifications can be made therein without departing from the scope of the inventions defined by the appended claims.

What is claimed is:

1. An apparatus for converting cellulosic material into glucose, comprising:

a first reaction vessel;

an attritor, the attritor being in fluid communication with the first reaction vessel;

a first filter means, the first filter means being in fluid communication with the attritor and the first reaction vessel;

a second filter means, the second filter means being in fluid communication with the first filter means and the first reaction vessel;

a cellobiose reactor, the cellobiose reactor being in fluid communication with the second filter means; and a third filter means, the third filter means being in fluid communication with the cellobiose reactor and the first reaction vessel.

2. The apparatus of claim 1, wherein the first filter means is a microfilter.

3. The apparatus of claim 1, wherein the second filter means is an ultrafilter.

4. The apparatus of claim 1, wherein the third filter means is a reverse osmosis filter.

5. The apparatus of claim 1, further comprising:

a second reaction vessel, the second reaction vessel being in fluid communication with the third filter means; and a third reaction vessel, the third reaction vessel being in fluid communication with the second reaction vessel.

* * * * *